United States Patent [19]
Farren et al.

[11] Patent Number: 4,667,515
[45] Date of Patent: May 26, 1987

[54] PIPELINE INSPECTION

[75] Inventors: John Farren, Harwell; Roger D. Watkins, Wantage, both of England

[73] Assignee: United Kingdom Atomic Energy Authority, London, England

[21] Appl. No.: 802,726

[22] Filed: Nov. 29, 1985

[30] Foreign Application Priority Data
Dec. 5, 1984 [GB] United Kingdom ............... 8430701

[51] Int. Cl.⁴ .............................................. G01N 29/00
[52] U.S. Cl. ...................................... 73/601; 73/32 R; 73/61 R
[58] Field of Search ............. 73/601, 570, 61 R, 32 R

[56] References Cited
U.S. PATENT DOCUMENTS
4,239,590 12/1980 Prough ............................. 73/32 R Primary Examiner—Anthony V. Ciarlante
Attorney, Agent, or Firm—William R. Hinds

[57] ABSTRACT

The nature of the flow pattern in a pipeline carrying both a liquid and a gas depends on the flow rates of the two phases. The flow pattern is characterized by measuring the void fraction or the average density along at least one chord across the pipeline (12) and by determining the distribution of liquid around the periphery of the pipe wall. The void fraction may be measured by the absorption of gamma rays from a source (14); while the peripheral distribution may be determined from the attenuation of ultrasonic plate waves propagating through sectors of the wall between transmitters (18) and receivers (20).

8 Claims, 5 Drawing Figures

PIPELINE INSPECTION

The invention relates to a method and an apparatus for the inspection of piplines to obtain information about their contents.

The invention is particularly applicable to the inspection of piplines carrying both a gas and a liquid, in which the nature of the flow depends upon the flow rates of the two components, ranging from small bubbles of gas dispersed in the liquid, to a thin peripheral layer of liquid around the wall of the pipeline.

According to the present invention there is provided a method of inspection of a pipeline carrying a liquid to characterise the contents thereof, the method comprising measuring the average density along at least one chord across the pipeline, and determining the distribution of liquid around the periphery of the pipeline.

The average density is preferably measured along a plurality of chords across the pipeline; and can be measured from the attenuation of gamma rays, X-rays or neutrons.

The peripheral distribution of the liquid is preferably determined by detecting the presence or absence of liquid at a plurality of locations around the periphery of the pipeline. This may be achieved using ultrasonic waves; either by causing ultrasonic compression waves to propagate through the wall of the pipeline and detecting the amplitude of the wave reflected at the inner surface of the wall; or by causing ultrasonic plate waves to propagate from a transmitter along a portion of the wall, circumferentially or axially, and detecting the amplitude of the wave received at a receiver spaced apart from the transmitter.

The invention also provides an apparatus for performing the method of inspection.

The invention will now be further described by way of example only and with reference to the accompanying drawings, in which.

When a gas-liquid mixture flows in a pipeline the two phases may define one of a variety of different patterns, the particular pattern depending on the physical properties of the liquid and the gas, the dimensions of the pipeline, and the flow rates of the two phases. The flow patterns are described for example in an article by Y. Taitel and A. E. Dukler, in A.I.Ch.E. Journal Vol. 22, No. 1 (January 1976); and an article by Y. Taitel, A. E. Dukler and D. Bornea in A.I.Ch.E. Journal VOl. 26, No. 3 (May 1980).

Referring to FIGS. 1a to d, the typical flow patterns where the gas and liquid flow upwardly in a vertical pipeline are shown. FIG. 1a shows "Bubble flow", in which the gas phase is distributed as discrete bubbles in a continuous liquid phase. FIG. 1b shows "Plug flow", in which most of the gas forms large bullet-shaped bubbles almost as wide as the pipeline. Between these large bubbles and the wall is a thin liquid film falling downwards. FIG. 1c shows "Churn flow", in which the flow is much more chaotic, parts of the liquid phase alternating in their direction of flow and churning around. FIG. 1d shows "Annular flow", which is characterised by the continuity of the gas phase along the centre of the pipeline, and in which the liquid phase forms a thin film on the wall, with a wavy surface. Part of the liquid phase may be in the form of droplets entrained in the gas, and in some circumstances these may form long foamy wisps.

Figure 1:
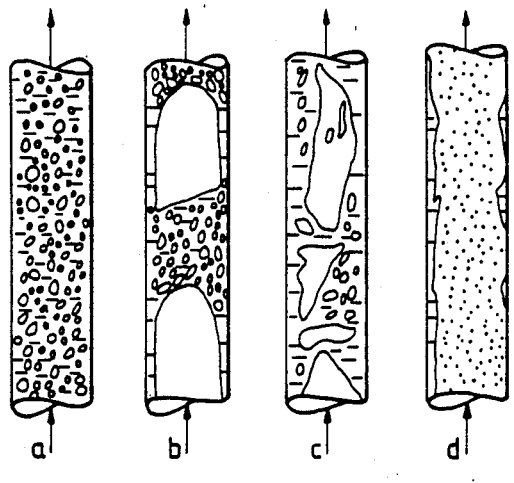
FIGS. 1a to 1d show diagrammatically flow patterns which can occur in a vertical pipeline.
Figure 2:
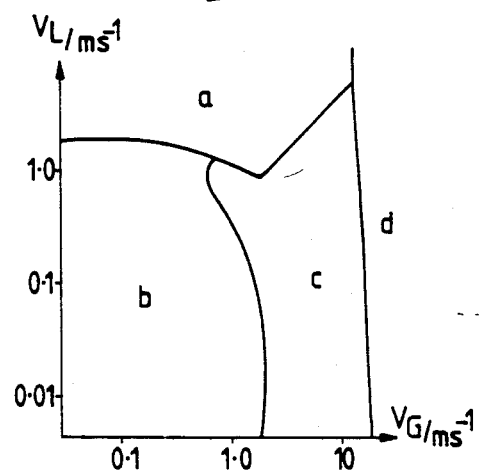
FIG. 2 shows graphically the gas and liquid flow velocities at which the flow patterns of FIGS. 1a to d occur.

Referring to FIG. 2, this indicates graphically the flow rates at which the flow patterns of FIG. 1 may occur, the graph axes representing the liquid superficial velocity ($V_L$) and the gas superficial velocity ($V_G$), and the letters a to d corresponding to the flow patterns of FIGS. 1a to d respectively (see May 1980 reference above). The superficial velocity means the volumetric flow rate divided by the cross-sectional area of the pipeline.

Figure 3:
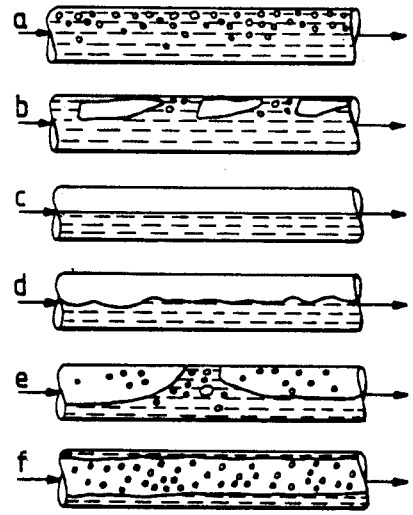
FIGS. 3a to 3f show diagrammatically flow patters which can occur in a horizontal pipe.
Figure 4:
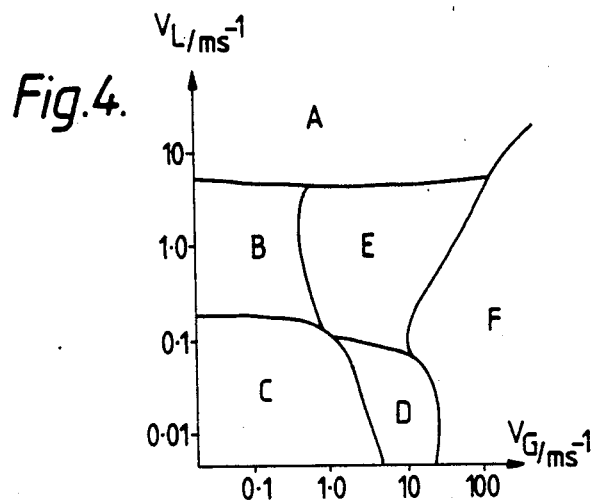
FIG. 4 shows graphically the gas and liquid flow velocities at which the flow patterns of FIGS. 3a to f occur.

Referring to FIGS. 3a to f, typical flow patterns are shown for a horizontal pipeline; and FIG. 4 indicates graphically the superficial velocities $V_L$ and $V_G$ at which the flow patterns of FIG. 3 may occur (see January 1976 reference above). The letters A to F in FIG. 4 correspond to the flow patterns of FIGS. 3a to f respectively. FIG. 3a shows "Bubble flow", similar to that of FIG. 1a except that the bubbles of gas tend to flow in the upper part of the pipeline. FIG. 3b shows "Plug flow", similar to that of FIG. 1b. FIG. 3a shows "Stratified flow", in which the liquid and gas phases are completely separate, and the interface is smooth. At higher gas velocities waves begin to form on the liquid surface, forming "Wavy flow" as shown in FIG. 3d, and at still higher gas velocities some of the waves become large enough to reach the top of the pipeline, forming "Slug flow" as shown in FIG. 3e. These large waves or slugs are often frothy, and move along with the gas at high velocity. FIG. 3f shows "Annular flow", which occurs at still greater gas velocities and is similar to that of FIG. 1d, differing in that the liquid film tends to be thicker at the bottom of the pipeline than the top.

The flow patterns described above have hitherto principally been studied using optical techniques, in transparent pipelines. Such techniques are obviously inapplicable to practical pipelines for example for oil and natural gas mixtures, which are of steel with a wall thickness of over 10 mm.

Figure 5:
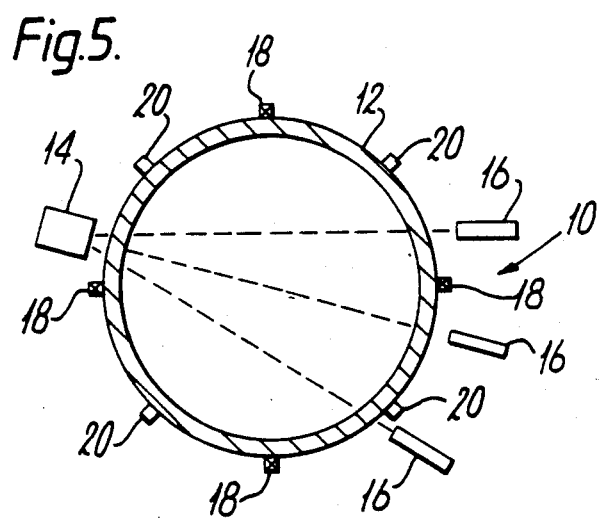
FIG. 5 shows diagrammatically an apparatus for inspection of a pipeline.

Referring now to FIG. 5, an apparatus 10 is shown for characterising the nature of the flow inside a pipeline 12, the pipeline 12 being shown in cross-section. The apparatus 10 comprises a gamma ray source 14 arranged to cause three beams of gamma rays to traverse the pipeline 12 along respective chords (shown as broken lines), and three gamma-ray detectors 16 arranged to detect the rays after their passage through the pipeline 12. The apparatus 10 also comprises four ultrasonic transmitters 18 and four ultrasonic receivers 20 mounted on the outside of the pipeline 12 equally spaced around its circumference, each receiver 20 being midway between two transmitters 18. Each transmitter 18 when energised causes ultrasonic plate waves (similar to a Lamb wave) to propagate in both directions around the wall of the pipeline 12, to be detected by the adjacent receivers 20. If a liquid layer of thickness greater than a few millimeters is present on the portion of wall through which propagation of the plate waves is taking place then mode conversion of the waves will occur, compression waves being generated in the liquid and the amplitude of the plate wave decreasing to zero within a propagation distance of a few wavelengths.

In operation of the apparatus 10 the gamma ray source 14 produces the three beams continuously and each of the three detectors 16 gives a continuous indication of the degree of absorption along the respective chord, and hence of the average density (or the void fraction) of the pipeline contents along the chord. Diametrical pairs of transmitters 18 are excited alternately, the amplitude of the signals detected by the receivers 20 indicating the presence or absence of a liquid layer on the portion of pipeline wall between the transmitter 18 and the receiver 20. Inspection of the indications given by the gamma ray detectors 16 and those given by the ultrasonic receivers 20 thus enables the distribution of liquid and gas within the pipeline 12, and its temporal variations, and so the nature of the flow pattern, to be determined. The apparatus 10 is non-invasive, and involves no modifications to the pipeline 12 itself, and so is applicable to practical pipelines 12.

It will be appreciated that the number of chords along which the degree of absorption is measured might be fewer or more than three; that the orientation of the chords might be different from those shown in the Figure; and that the source 14 of gamma rays might be replaced by a source of x-rays or of neutrons, the detectors 16 being changed accordingly.

It will be further appreciated that the numbers of ultrasonic transmitters 18 and receivers 20 might differ from that described; and the transmitters 18 might be arranged to cause the plate waves to propagate along the length of the pipeline 12 rather than circumferentially, the receivers 20 being repositioned accordingly.

A modification of the apparatus 10 includes two sets of transmitters 18 and receivers 20 spaced apart along the pipeline 12. Correlation of the indications given by the two sets enables the rate of movement of, for example, a liquid plug along the pipeline to be determined.

We claim:

1. A method of inspection of an opaque-walled pipeline carrying a gas and a liquid to characterise the cntents thereof, the method comprising measuring the average density along at least one chord across the pipeline, and determining the distribution of liquid around the periphery of the pipeline.

2. A method as claimed in claim 1 wherein the average density is measured along a plurality of chords across the pipeline.

3. A method as claimed in claim 1 wherein the peripheral distribution of the liquid is determined by detecting the presence or absence of liquid at a plurality of locations around the periphery of the pipeline.

4. A method as claimed in claim 3 wherein the peripheral distribution is determined by causing ultrasonic compression waves to propagate through the wall of the pipeline and detecting the amplitude of the wave reflected at the inner surface of the wall.

5. A method as claimed in claim 3 wherein the peripheral distribution is determined by causing ultrasonic plate waves to propagate from a transmitter along a portion of the wall, and detecting the amplitude of the wave received at a receiver spaced apart from the transmitter.

6. A method as claimed in claim 1 wherein said determining is by an ultrasonic technique.

7. Apparatus for inspecting an opaque-walled pipeline carrying a gas and a liquid to characterise the contents thereof, comprising means for measuring the average density along at least one chord across the pipeline, and means for determining the distribution of liquid around the periphery of the pipeline.

8. Apparatus as claimed in claim 7 wherein said means for determining uses an ultrasonic technique.

* * * * *